United States Patent
Maki, Jr. et al.

(10) Patent No.: US 7,677,104 B2
(45) Date of Patent: Mar. 16, 2010

(54) ACOUSTIC TRANSDUCER SYSTEM FOR NONDESTRUCTIVE TESTING OF CEMENT

(75) Inventors: Voldi E. Maki, Jr., Austin, TX (US); John Jeffery Moon, Jr., Tulsa, OK (US)

(73) Assignee: Chandler Instruments Company, LLC, Broken Arrow, OK (US)

( * ) Notice: Subject to any disclaimer, the term of this patent is extended or adjusted under 35 U.S.C. 154(b) by 492 days.

(21) Appl. No.: 11/613,816

(22) Filed: Dec. 20, 2006

(65) Prior Publication Data

US 2008/0148852 A1 Jun. 26, 2008

(51) Int. Cl.
*G01N 29/24* (2006.01)
*G01N 29/32* (2006.01)

(52) U.S. Cl. .............................. 73/632; 73/801; 73/803; 73/594; 310/327

(58) Field of Classification Search ..................... 73/632
See application file for complete search history.

(56) References Cited

U.S. PATENT DOCUMENTS

| | | | |
|---|---|---|---|
| 4,045,999 A | 9/1977 | Palmer | |
| 4,073,193 A | 2/1978 | Mastandrea | |
| 4,254,479 A | 3/1981 | Wiley | |
| 4,259,868 A | 4/1981 | Rao et al. | |
| 4,380,930 A | 4/1983 | Podhrasky et al. | |
| 4,567,765 A | 2/1986 | Rao et al. | |
| 4,571,988 A | 2/1986 | Murphy, Jr. | |
| 4,625,542 A | 12/1986 | Nelson | |
| 4,843,598 A | 6/1989 | Medlin | |
| 5,001,676 A | 3/1991 | Broding | |
| 5,089,989 A | 2/1992 | Schmidt et al. | |
| 5,625,140 A | 4/1997 | Cadet et al. | |
| 5,763,766 A | 6/1998 | Robinson | |
| 5,763,773 A | 6/1998 | Birchak et al. | |
| 5,894,181 A | 4/1999 | Imlach | |
| 5,992,223 A | 11/1999 | Sabins et al. | |
| 6,070,465 A | 6/2000 | Maki, Jr. | |
| 6,112,599 A | 9/2000 | Maki, Jr. | |
| 6,166,998 A * | 12/2000 | Hare et al. | 367/176 |
| 6,345,535 B1 | 2/2002 | Sabins et al. | |
| 6,483,777 B1 | 11/2002 | Zeroug | |
| 6,691,559 B2 | 2/2004 | Robinson | |
| 6,941,819 B1 | 9/2005 | Maki, Jr. et al. | |

* cited by examiner

*Primary Examiner*—Hezron Williams
*Assistant Examiner*—Rose M Miller
(74) *Attorney, Agent, or Firm*—Fellers, Snider, Blankenship, Bailey & Tippens

(57) ABSTRACT

An acoustic transducer system for use in the measurement of longitudinal sound velocity in a cement sample that is maintained at high temperature and pressure. The acoustic assembly is separate from the end plugs to optimize acoustic coupling between the individual elements of the assembly, to increase the amplitude and consistency of the acoustic signal and to provide an ability to replace the transducers as a separate assembly. The transducer includes an acoustic transmission line and utilizes a pressure isolation method to optimize the material and the manufacturing process to enhance the acoustic signal required for the measurement. The transducer assembly includes a high temperature piezoelectric ceramic and a load mass that improve the signal amplitude and provide the required electrical connections. The transducer improves the ability to measure the longitudinal wave velocity in a cement sample at elevated temperature and pressure for determining the sample's compressive strength.

2 Claims, 2 Drawing Sheets

ACOUSTIC TRANSDUCER SYSTEM FOR NONDESTRUCTIVE TESTING OF CEMENT

FIELD OF THE INVENTION

A system for transmitting acoustic energy into a cement sample, wherein the system includes an ultrasonic port received in a receptacle in an end plug. More particularly, the ultrasonic port defines a flat surface for contacting a piezoelectric ceramic transducer for acoustic excitation without use of a coupling agent.

BACKGROUND OF THE INVENTION

Ultrasonic cement analyzers ("UCA") are well known in the art. A typical UCA provides a number of advantages over alternative methods for measuring or estimating the characteristics of a particular cement sample. A particularly compelling advantage is the ability of the UCA to perform nondestructive measurements at elevated temperature and pressure such as may be found in oil field applications.

The UCA was developed to measure the compressive strength of a cement slurry as the cement sets while subjected to oil field temperatures and pressures. A typical UCA consists of a high temperature, high pressure vessel, a heating jacket capable of heating rates up to 5.6° C. (10° F.) per minute, up to 204° C. (400° F.) and pressures to 138.0 MPa (20,000 psi).

A typical UCA utilizes a pair of ultrasonic transducers to measure transit time of an acoustic signal transmitted through the slurry as it sets. Set time and compressive strength are calculated from the measured transit time via empirically developed equations. U.S. Pat. Nos. 4,259,868 and 4,567,765 disclose UCAs in detail and are incorporated herein by reference.

The operating temperature of a typical UCA, however, is limited by the use of a ceramic with a Curie temperature of typically 300° C., a coupling coefficient of 0.71 and an impedance of $35 \times 10^6$ MKS Rayls. The limit on operating temperature of the standard UCA has typically been 200° C. With the need to evaluate cement at temperatures up to 316° C. (600° F.), a different type of piezoelectric ceramic is desirable.

Piezoelectric ceramics with a high Curie temperature are available. However, a problem associated with using piezoelectric ceramics in a UCA is that the typical coupling coefficient of the ceramic decreases as the Curie temperature increases. Because of the already low signal level and the lower sensitivity of high temperature piezoelectric ceramic, an improvement in the mechanical design of the UCA is desirable to increase the signal amplitude.

The piezoelectric ceramic in a typical UCA is mated to an interior of a plug at the bottom of a flat bottom hole approximately 2.5 inches deep. To achieve good signal amplitude in the measurement, the bottom of the hole should be extremely flat to couple acoustic energy from the transducer into the cement. Manufacturing and maintaining this flat surface presents difficulties. High temperature grease is typically used to compensate for inadequacies of the acoustic coupling. Over time this grease tends to degrade due to heat, which results in loss of signal. The thickness of the metal separating the piezoelectric ceramic from the cement acts as a narrow band filter that limits the measurement to a narrow range of frequencies.

It is therefore desirable to produce a transducer for use in a UCA that operates at higher temperature and produces higher signal amplitude to obtain accurate transit time measurements.

SUMMARY OF THE INVENTION

The acoustic transducer system of the invention is used to measure longitudinal sound velocity in a cement sample maintained at high temperature and pressure. The acoustic transducer system is adapted for use with a conventional ultrasonic cement analyzer (UCA), but is separate from the end plugs of the UCA to optimize acoustic coupling between the individual elements of the system, which increases the amplitude and consistency of the acoustic signal and provides an ability to replace the transducers as a separate assembly. The transducer assembly of the invention includes an acoustic transmission line and utilizes a pressure isolation method to optimize the material and the manufacturing process to enhance the acoustic signal required for the measurement. The transducer assembly includes a high temperature piezoelectric ceramic and a load mass that improves the signal amplitude and provides the required electrical connections. The transducer assembly improves the ability to measure the longitudinal wave velocity in a cement sample at elevated temperature and pressure for determining the sample's compressive strength.

More particularly, the invention relates to a transducer assembly for an ultrasonic cement analyzer that includes an acoustic port having a flat upper surface, a piezoelectric ceramic having a flat upper surface and flat lower surface in communication with said flat upper surface of said acoustic port, a back mass having a flat upper surface and a flat lower surface in communication with the flat upper surface of said ceramic transducer and a tension bolt for securing said acoustic port, said ceramic transducer, and said back mass tightly together. In a preferred embodiment, the acoustic port functions as a negative electrode and the back mass functions as a positive electrode.

An electrical communicator, such as a spring, is located between and in electrical communication with the electrical connector and the back mass. The flat surfaces have a minimal surface variance, preferably 20 microns or less, to promote acoustic coupling between said acoustic port, said piezoelectric ceramic, and said back mass without a need for a coupling agent.

The acoustic port is adapted to be received in an end plug of a pressure vessel. The acoustic port defines an annulus that acoustically isolates a signal from the end plug.

An outer surface of the acoustic port is tapered for forming a metal-to-metal seal with the end plug.

The acoustic transducer system of the invention improves signal quality by placing critical elements where they can be processed properly. The invention allows for the easy use of materials with the best acoustic properties. The use of a transmission line greatly increases the bandwidth available for the acoustic signal, e.g., not only can the ~500 kHz used in the standard UCA be used but also much lower frequencies may be utilized in the measurement of transit time.

DETAILED DESCRIPTION OF THE PREFERRED EMBODIMENTS

Before explaining the present invention in detail, it is important to understand that the invention is not limited in its application to the details of the construction illustrated and the steps described herein. The invention is capable of other embodiments and of being practiced or carried out in a variety of ways. It is to be understood that the phraseology and terminology employed herein is for the purpose of description and not of limitation.

Figure 1:
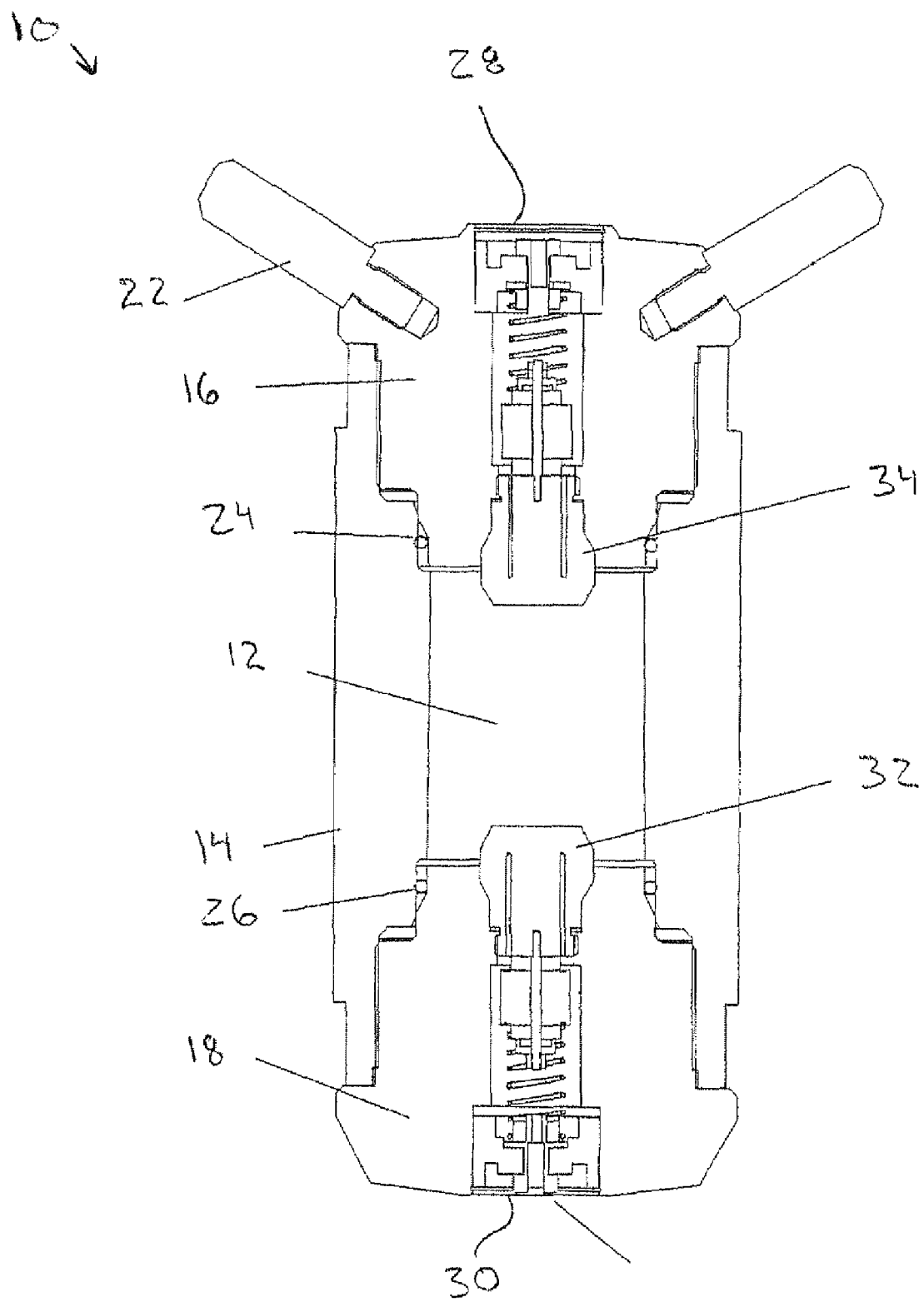
FIG. 1 provides a cross-sectional side view of the ultrasonic cement analyzer cell having a transducer assembly mounted therein.

Referring first to FIG. 1, shown is an example of a pressure vessel 10 for a preferred Ultrasonic Cement Analyzer. Cement is confined in cavity 12, which is defined by cell housing or cylinder wall or vessel wall 14, upper end plug 16 and by lower end plug 18. Pressure vessel 10 may be lifted using handles 22. Seals 24 and 26, typically constructed of elastomer and metal, form a seal between wall 14 and end plugs 16 and 18. Upper electrical connection 28 is located on an upper surface of upper end plug 16. Lower electrical connection 30 is located on a lower end of lower end plug 18. Upper electrical connection 28 is typically for a receiver and lower electrical connection 30 is for a transmitter.

Acoustic energy propagating from lower acoustic port 32 passes through the cement to upper acoustic port 34. The transit time of this signal is used to compute the compressive strength of the cement using industry accepted equations that relate transit time to cement compressive strength. Acoustic energy also travels from lower port 32 through lower end plug 18 through vessel wall 14 to upper end plug 16 and into upper acoustic port 34. The design of the vessel makes this path of adequate length and with enough attenuation that any signal propagating along this path does not contaminate the measurement of the signal passing through the cement. In previous UCA designs, the acoustic function performed by acoustic ports 32 and 34 were simply a protrusion into cement with a diaphragm thickness of approximately 0.3 inches to withstand the pressure with a longitudinal wave transducer inserted in the air space within the plug opposite the cement and pressed against the diaphragm.

Figure 2:
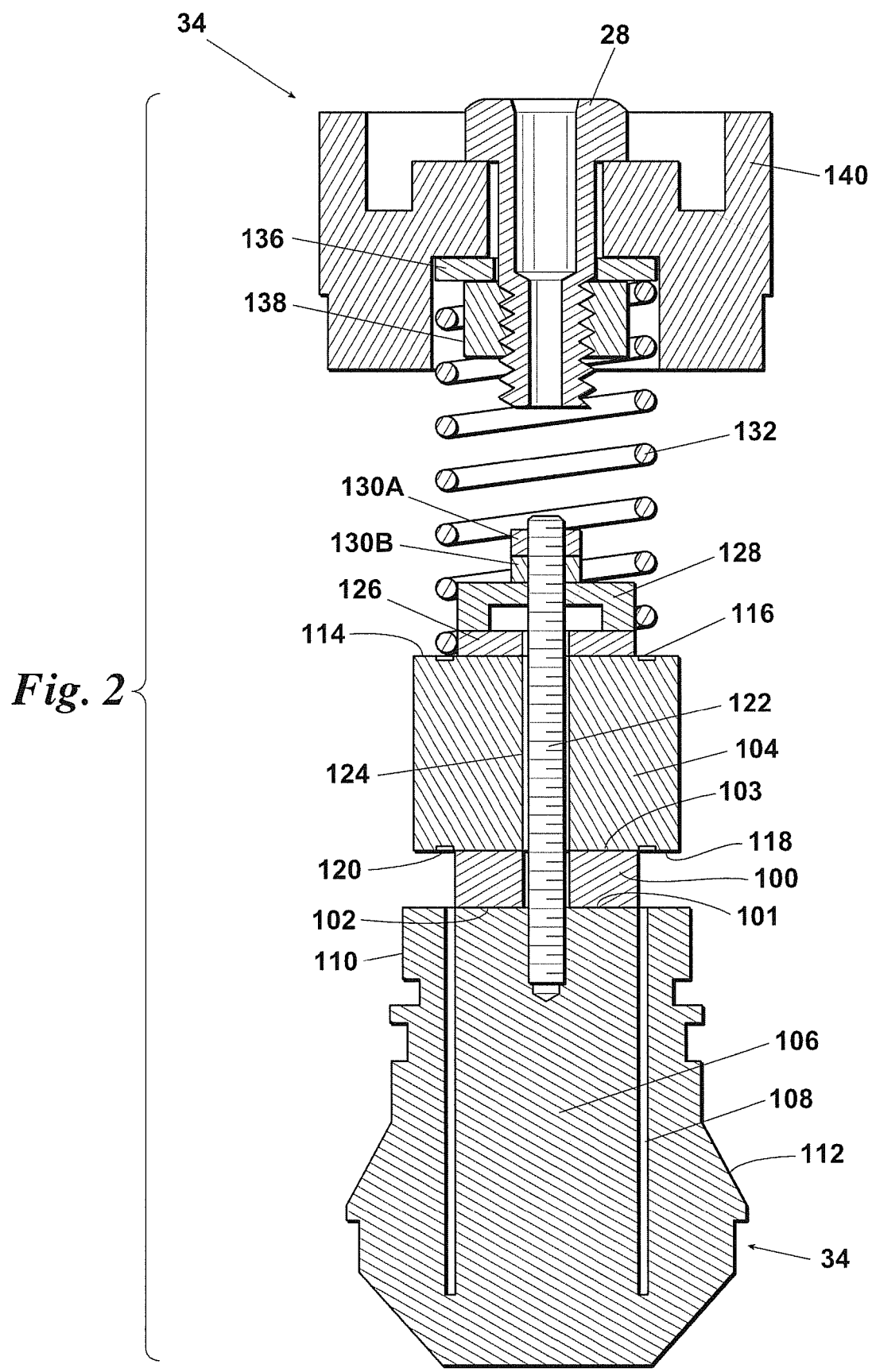
FIG. 2 provides an enlarged cross-sectional side view of the transducer assembly of FIG. 1.

An enlarged view of the transducer assembly and upper acoustic port 34 are shown in FIG. 2. The lower assembly that includes lower acoustic port 32 is identical in function. Therefore, it should be understood that all references to "upper" components are also applicable to "lower" components. A piezoelectric ceramic is designated 100. One type of ceramic used in this application is K-81 (Keramos), which is a modified lead metaniobate material having a Curie temperature of 400° C. It has an acoustic impedance of $19 \times 10^6$ MKS Rayls and a planar coupling coefficient of 0.3. Various other materials may be used depending upon the temperature requirements.

Lower contact surface 102 on the piezoelectric ceramic 100 contacting the upper surface 101 of the acoustic port 34 are lapped flat to approximately 20μ inches as are the upper surface 103 of the piezoelectric ceramic 100 and lower surface 118 of back mass 104. While a surface flatness having a variance of 100μ inches to 500μ inches was found to be acceptable, best results were achieved when surfaces 101, 102, 103 and 118 are flat, having a surface variance of approximately 20μ inches or less. The accuracy of contact surfaces 102 eliminates the need for any coupling agent to promote acoustic coupling between the components.

Upper acoustic port 34 acts as the ground electrode for ceramic transducer 100. Back mass 104 functions as a positive electrode. The acoustic signal passes through center 106 of upper acoustic port 34, which acts as a transmission line for the acoustic signal. This acoustic path is isolated from the exterior of upper acoustic port 34 by annulus 108, preferably created by using an electrical discharge machining technique. Annulus 108 acoustically isolates the signal from upper end plug 16 until the signal propagates to the end of upper acoustic port 34, which is in contact with the cement. The isolation is required to separate in time and amplitude the signal that could travel through vessel wall 20 of pressure vessel 10. The isolation also decreases the total signal that is allowed to leak into pressure vessel 10. Upper acoustic port 34 is held in place in upper end plug 16 by left hand threads 110. Metal-to-metal seal 112 maintains pressure in within cavity 12.

Upper acoustic port 34 is preferably made from a metal such as titanium because of its strength and its acoustic impedance. Titanium has an acoustic impedance of $27.3 \times 10^6$ MKS Rayls as opposed to stainless steel with an impedance of $45.7 \times 10^6$ MKS Rayls. The lower impedance improves both the coupling of energy from ceramic transducer 100 to upper acoustic port 34 as well as improves the coupling of the signal from upper acoustic port 34 to the cement slurry. The improved coupling increases the signal level in the measurement.

Both the upper surface 114 and lower surface 118 of the back mass 104 have a cut, i.e., upper cut 116 of upper surface 114 and lower cut 120 of lower surface 118 beginning at a diameter of piezoelectric ceramic 100 that is one half the distance to the edge of the mass 104, approximately 0.01 inches deep. This cut, i.e., cut 116, 118, reduces the metal that must be removed in the lapping process and allows the outer edge to stabilize the part while lapping to more easily obtain a flat surface. Back mass 104 is typically made from stainless steel although other high density materials may be used. Upper acoustic port 34, ceramic transducer 100, and back mass 104 are clamped tightly together using tension bolt or threaded rod 122 with insulated sleeve 124. Since back mass 104 functions as the positive electrode and threaded rod 122 functions as ground, electrical isolation is required. Upper surface 114 of back mass 104 is preferably lapped to approximately 20μ inches surface flatness, as are both surfaces of ceramic insulator 126, and a lower surface of load distribution washer 128. Double nuts 130a and 130b are used to apply tension to the stack of components and to prevent any movement over time. Spring 132 provides both support for upper electrical connection 28 and functions as an electrical conductor for the positive connection to ceramic transducer 100. Spring 132 contacts upper washer 136, which is preferably a lock washer, and which is contacted by retaining nut 138. Retaining nut 138 holds upper electrical connector 28 onto ceramic insulator 140. The ground path is through upper acoustic port 34 and upper end plug 16.

In addition to providing the ability to improve the signal quality by placing critical elements where they can be processed properly, the improved design of the invention allows for the easy use of materials with the best acoustic properties. By modifying acoustic ports 32, 34 from a diaphragm to a transmission line, the bandwidth of the acoustic signal was greatly increased. The invention allows the measurement of transit time at frequencies ranging from 500 kHz used in the standard UCA, to frequencies as low as 113 kHz.

Thus, the present invention is well adapted to carry out the objectives and attain the ends and advantages mentioned above as well as those inherent therein. While presently preferred embodiments have been described for purposes of this disclosure, numerous changes and modifications will be apparent to those of ordinary skill in the art. Such changes and modifications are encompassed within the spirit of this invention as defined by the claims.

What is claimed is:

1. A transducer assembly for an ultrasonic cement analyzer comprising:

an acoustic port having an external flat surface;

a ceramic transducer having a first flat surface and a second flat surface, said second flat surface in communication with said external flat surface of said acoustic port;

a back mass having a first flat surface and a second flat surface, said second flat surface of said back mass in communication with the first flat surface of said ceramic transducer;

a tension bolt for securing said acoustic port, said ceramic transducer, and said back mass tightly together;

an electrical connector in electrical communication with said back mass;

wherein said flat surfaces have a minimal surface variance to promote acoustic coupling between said acoustic port, said ceramic transducer, and said back mass;

wherein said acoustic port is adapted to be received in an end plug of a pressure vessel; and wherein said acoustic port defines an annulus that acoustically isolates a signal from said end plug.

2. The transducer assembly according to claim 1 wherein:

an outer surface of said acoustic port is tapered for forming a metal-to-metal seal with said end plug.

\* \* \* \* \*